United States Patent [19]
Tanner et al.

[11] Patent Number: 5,514,437
[45] Date of Patent: May 7, 1996

[54] ARTIFICIAL TANNING COMPOSITIONS HAVING IMPROVED STABILITY

[75] Inventors: Paul R. Tanner, Maineville; Larry R. Robinson, Lebanon, both of Ohio

[73] Assignee: The Procter & Gamble Company, Cincinnati, Ohio

[21] Appl. No.: 219,053

[22] Filed: Mar. 29, 1994

[51] Int. Cl.$^6$ ................................................. A61K 7/021
[52] U.S. Cl. ............................ 424/63; 424/59; 424/60
[58] Field of Search .............................. 424/63, 60, 59

[56] References Cited

U.S. PATENT DOCUMENTS

| | | | |
|---|---|---|---|
| 2,274,725 | 3/1942 | Meeker et al. | 424/59 |
| 2,949,403 | 8/1960 | Andreadis . | |
| 3,177,120 | 4/1965 | Black et al. | 424/59 |
| 3,184,388 | 5/1965 | Kalopissis | 424/59 |
| 3,272,713 | 9/1966 | Runge | 424/59 |
| 3,920,808 | 11/1975 | Fusaro | 424/59 |
| 4,145,413 | 3/1979 | Usdin et al. | 424/63 |
| 4,293,543 | 10/1981 | Cotte et al. | 424/59 |
| 4,419,343 | 12/1983 | Pauly | 424/59 |
| 4,434,154 | 2/1984 | McShane | 424/60 |
| 4,831,943 | 5/1989 | Grollier et al. | 424/59 |
| 4,847,267 | 7/1989 | Deckner et al. | 514/311 |
| 5,100,660 | 3/1992 | Hawe et al. | 424/78.35 |
| 5,221,530 | 6/1993 | Janchitraponveg et al. | 424/70 |
| 5,232,688 | 8/1993 | Ziegler et al. | 424/59 |
| 5,302,378 | 4/1994 | Crotty et al. | 424/59 |

FOREIGN PATENT DOCUMENTS

| | | | |
|---|---|---|---|
| 90/61950 | 5/1991 | Australia | A61K 7/02 |
| CA72(20):103635B | 1969 | Czechoslovakia . | |
| 227012 | 7/1987 | European Pat. Off. | A61K 7/00 |
| 456545 | 4/1991 | European Pat. Off. | A61K 7/42 |
| 547864 | 6/1993 | European Pat. Off. | A61K 7/42 |
| 622070A1 | 11/1994 | European Pat. Off. | A61K 7/42 |
| 34227937 | 8/1994 | Japan | A61K 7/42 |
| 98(16):132150g | 10/1982 | Spain | A61K 62/4 |
| 83-825600/47 | 1/1983 | U.S.S.R. | A61K 7/00 |
| WO92/17159 | 10/1992 | WIPO | A61K 7/42 |
| WO93/09215 | 5/1993 | WIPO | C11D 3/04 |

OTHER PUBLICATIONS

Technical Bulletin–Salcare SC 92 for Cosmetic/Personal Care applications, Allied Colloids, Suffolk, VA–Undated.
M. S. Balsam et al., (ed.) Cosmetic Science and Technology 2nd edition, Dec. 10, 1973, vol. 1, pp. 293–305 Wiley–Interscience, New York.
Merck German Technical Data sheet, Nov. 24, 1993.
Kawashima et al., "Nonenzymatic Browning Reactions of Dihydroxyacetone with Amino Acide or Their Esters", Agric. Biol. Chem., 44(7), 1595–1599 (1980).
Ingredient label from packaging, Bain de Soleil Tanning Creme, copyright 1993.
A. Meybeck, "A Spectroscopic Study of the Reaction Products of Dihydroxyacetone with Amine Acids". J. Soc. Cosmet. Chem., 28, 25–35 (1977).
E. Wittgenstein et al., "Reaction of Dihydroxyacetone (DHA) with Human Skin Callus and Amino Compounds", J. Invest. Derm., 23, 283–286 (1961).
M. F. Bobin et al., "Effects of Color Adjuvants on the Tanning Effect of Dihydroxyacetone", J. Soc. Cosmet. Chem., 35, 265,272 (Aug. 1984).
Ingredient label from Elizabeth Arden's Spa for the Sun Self Tanner SPF 15 Product, no copyright date available.
The Merck Index, Tenth Edition, 1983, Entry 8476.
V. R. Usdin, "Artificial Tanning Preparations",Cosmetics and Toiletries, vol. 91, Mar. 1976 pp. 29–32.
J. Buchter et al., "The Reaction of Dihydroxyacetone with Proteins", American Perfumer, Dec. 1960, pp. 46–48.
N. Kanas et al., "Factors Influencing the Tanning Effect of Dihydroxyacetone of the Skin",American Perfumer, Nov. 1960, pp. 33–34.
M. Fleming et al., "Chemistry of Browning Reaction", The Sugar Journal, Apr. 1971, pp. 21–27.
K. Laden et al., "The Reaction of $\alpha$–Hydroxymethyl Ketones with Skin and Amino Acids", J. Soc. Cosmetic Chemists, 16, 777–782 (1965).

Primary Examiner—Shelley A. Dodson
Attorney, Agent, or Firm—Anthony D. Sabatelli; David K. Dabbiere

[57] ABSTRACT

The present invention relates to artificial tanning compositions having improved stability. These compositions comprise dihydroxyacetone, a salt selected from the group consisting of metabisulfite salts, sulfite salts, hydrogen sulfite salts, and mixtures thereof. These compositions are useful for imparting an artificial tan to human skin. In further embodiments, these compositions also comprise a sunscreen agent and are also useful for providing protection from the harmful effects of ultraviolet radiation.

19 Claims, No Drawings

ND TANNING COMPOSITIONS
ARTIFICIAL TANNING COMPOSITIONS HAVING IMPROVED STABILITY

The present invention relates to compositions useful for providing an artificial tan to human skin. These compositions exhibit improved chemical and physical stability. These compositions comprise dihydroxyacetone, a salt selected from the group consisting of metabisulfite salts, sulfite salts, and hydrogen sulfite salts, and mixtures thereof, and a topical carrier. In further embodiments these compositions also comprise a sunscreen agent and are useful for protecting the skin from the harmful effects of ultraviolet radiation.

BACKGROUND OF THE INVENTION

A sun-tanned appearance is a symbol of a healthy, dynamic, and active life. Yet, the damaging effects of sunlight and other sources of ultraviolet radiation on the skin are well documented. These effects are cumulative and potentially serious, and include sunburn, skin cancer, and premature aging of the skin. These effects associated with exposure to ultraviolet radiation are more fully discussed in DeSimone, "Sunscreen and Suntan Products", *Handbook of Nonprescription Drugs*, 7th Ed., Chapter 26, pp. 499–511 (American Pharmaceutical Association, Washington, D.C; 1982); Grove and Forbes, "A Method for Evaluating the Photoprotection Action of Sunscreen Agents Against UV-A Radiation", *International Journal of Cosmetic Science*, 4, pp. 15–24 (1982); and U.S. Pat. No. 4,387,089, DePolo, issued Jun. 7, 1983; the disclosures of all of which are incorporated herein by reference in their entirety.

Sunscreens are the most common agents used for sun protection. However, sunscreens also have the disadvantage of preventing or greatly diminishing the cosmetically desirable tanning response. Thus, if an individual uses a sunscreen for protection from ultraviolet radiation, he or she does so at the expense of foregoing a tanned appearance. Furthermore, even if an individual is willing to accept the risks associated with exposure to ultraviolet radiation to obtain a tan, there are situations in which it may not be practical or even possible to do so because of time constraints, weather conditions, etc. Therefore, it would be highly desirable to develop products for providing a tanned appearance to the skin, whenever desired without the need for exposure to ultraviolet radiation.

It is generally known that dihydroxyacetone, when applied topically to human skin, will produce a tanned appearance, i.e. an artificial tan. U.S. Pat. No. 4,708,865, to Turner, issued Nov. 24, 1987 describes the use of hydroalcoholic solutions of dihydroxyacetone for tanning the skin; U.S. Pat. No. 4,466,805, to Welters, issued Aug. 21, 1984 describes hair and skin coloring formulations containing dihydroxyacetone; and U.S. Pat. No. 2,949,403, to Andreadis et al., issued Aug. 16, 1960 describes artificial tanning formulations containing dihydroxyacetone in an oleaginous base.

Dihydroxyacetone is relatively sensitive to heat, light, and moisture. It is known that products containing dihydroxyacetone generally have a short shelf life, tending to darken and develop disagreeable off-odors over time, with a concomitant loss of product performance. Dihydroxyacetone can react with other ingredients in a formulation, especially with nitrogen-containing compounds, such as amines, amino acids, and the like. In fact, without being limited by theory, dihydroxyacetone is believed to provide an artificial tan to human skin by its reaction with the nitrogen containing proteins of the skin. See L. Goldman et al., "Investigative Studies with the Skin Coloring Agents Dihydroxyacetone and Glyoxal", *The Journal of Investigative Dermatology*, vol. 35, pp. 161–164 (1960); E. Wittgenstein et al., "Reaction of Dihydroxyacetone (DHA) with Human Skin Callus and Amino Compounds", *The Journal of Investigative Dermatology*, vol. 36, pp. 283–286 (1961); and A. Meybeck, "A Spectroscopic Study of the Reaction Products of Dihdyroxyacetone With Amino Acids", *J. Soc. Cosmet. Chem.*, 25–35 (1977); all of which are incorporated by reference herein in their entirety. This incompatibility of dihydroxyacetone with nitrogen containing compounds has limited the formulation scope of artificial tanning products in the past.

Conventional stablilizing agents and antioxidants such as BHA, BHT, and vitamin E are ineffective for stabilizing artificial tanning compositions containing dihydroxyacetone. Surprisingly, it is found in the present invention that certain salts such as metabisulfite salts, sulfite salts, and hydrogen sulfite salts greatly enhance the stability of artificial tanning compositions containing dihydroxyacetone. The use of metabisulfite salts as anti-oxidants is known in the pharmaceutical area, however, their use has typically been limited to extremely low levels, e.g. 0.005%. In the present invention, it is found that much higher levels of salts such as metabisulfite, sulfite, and hydrogen sulfite salts, i.e. levels in the range from about 0.025% to about 5%, provide an unexpected enhancement of stability. This enhanced stability translates into benefits such as increased product shelf life, good product performance, maintenance of the aesthetic characteristics of the product, i.e. less discoloration and off-odors, and better user acceptance.

It is therefore an object of the present invention to provide artificial tanning compositions useful for imparting an artificial tan to human skin.

It is another object of the present invention to provide artificial tanning compositions which exhibit improved chemical and physical stability.

It is another object of the present invention to provide artificial tanning compositions which have good color development characteristics such as providing a natural looking and rapidly developing tan.

It is another object of the present invention to provide artificial tanning compositions useful for both providing an artificial tan to human skin and for protecting human skin from the harmful effects of ultraviolet radiation.

It is another object of the present invention to provide a method for artificially tanning human skin.

It is another object of the present invention to provide a method for artificially tanning human skin and for providing protection from the harmful effects of ultraviolet radiation.

These and other objects of this invention will become apparent in light of the following disclosure.

SUMMARY OF THE INVENTION

The present invention relates to an artificial tanning composition having improved stability comprising:
 (a) from about 0.1% to about 20% dihydroxyacetone,
 (b) from about 0.025% to about 5% of a salt selected from the group consisting of metabisulfite salts, sulfite salts, hydrogen sulfite salts, and mixtures thereof, and
 (c) a topical carrier.

All percentages and ratios used herein are by weight of the total composition and all measurements made are at 25° C., unless otherwise designated. The invention hereof can comprise, consist of, or consist essentially of, the essential as well as optional ingredients and components described herein.

DETAILED DESCRIPTION OF THE INVENTION

The compositions of the present invention are useful for providing an artificial tan to human skin. It is found that these compositions have improved chemical and physical stability and provide improved product integrity. These products also have good performance.

The term "chemical stability", as used herein, means that the various chemical components of the compositions, especially the dihydroxyacetone, do not exhibit appreciable breakdown or degradation. For example, the compositions of the present invention typically retain about 80% or more of the initially added dihydroxyacetone over about a three month period of time at room temperature. The term "physical stability", as used herein, means that the overall composition exhibits physical characteristics such as resistance to developing off-odors and resistance to discoloration and darkening. The term is further used herein to refer to maintenance of viscosity, resistance to syneresis, and in the case of emulsions, resistance to phase separation. For example, the compositions of the present invention typically maintain their physical stability for at least about a three month period of time at room temperature. The terms "chemical stability" and "physical stability" have been separately defined herein for convenience. Nevertheless, it is realized that these two types of stability phenomena are not necessarily distinct and that chemical stability can impact physical stability and vice versa.

The term "topical application", as used herein, means to apply or spread the artificial tanning compositions to or onto the surface of the skin.

The term "pharmaceutically-acceptable", as used herein, means that the compositions or components hereof so described are suitable for use in contact with human tissue without undue toxicity, incompatibility, instability, irritation, allergic response, and the like.

Dihydroxyacetone

The compositions of the present invention comprise from about 0.1% to about 20%, more preferably from about 2% to about 7%, and most preferably from about 3% to about 6% of dihydroxyacetone.

Dihydroxyacetone, which is also known as DHA or 1,3-dihydroxy-2-propanone, is a white to off-white, crystalline powder. This material can be represented by the chemical formula $C_3H_6O_3$ and the following chemical structure.

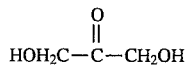

Dihydroxyacetone can exist as a mixture of monomers and dimers, with the dimers predominating in the solid crystalline state. Upon heating or melting, the dimers break down to yield the monomers. This conversion of the dimeric form to the monomeric form also occurs in aqueous solution. See The Merck Index, Tenth Edition, entry 3167, p. 463 (1983), and "Dihydroxyacetone for Cosmetics", E. Merck Technical Bulletin, 03–304 110, 319 897, 180 588; both of these references being incorporated herein by reference in their entirety. Dihydroxyacetone is commercially available from E. Merck (Darmstadt, Germany) and Gist-Brocades Food Ingredients, Inc. (King of Prussia, Pa.).

The scientific literature suggests that the reaction of dihydroxyacetone with the skin is similar to the Maillard Reaction. In this reaction, reducing sugars react with amino acids, proteins, and peptides to form various adducts which are ultimately converted into brown-colored compounds. See V. R. Usdin, Artificial Tanning Preparations, *Cosmetics and Toiletries*, vol. 91 pp. 29–32 (March 1976), this reference being incorporated herein by reference in its entirety. Without being limited by theory, it is believed that dihydroxyacetone reacts with the amino acids and amino groups of the skin keratin thereby forming the brown colored compounds which provide an artificial tan. It is believed that the process takes place in the outer layers of the epidermis and that the monomer form is responsible for this phenomenon.

Metabisulfite, Sulfite, and Hydrogen Sulfite Stabilizing Salts

The compositions of the present invention comprise from about 0.025% to about 5%, preferably from about 0.05% to about 5%, more preferably from about 0.05% to about 1%, even more preferably from about 0.1% to about 1%, and most preferably about 0.25% of a stabilizing, antioxidant salt selected from the group consisting of metabisulfite salts, sulfite salts, hydrogen sulfite salts, and mixtures thereof.

A metabisulfite salt contains the metabisulfite anion (also known as the pyrosulfite anion) which corresponds to the chemical formula $(S_2O_5)^{2-}$. A sulfite salt contains the sulfite anion which corresponds to the chemical formula $(SO_3)^{2-}$. A hydrogen sulfite salt contains the hydrogen sulfite anion (also known as the bisulfite anion) which corresponds to the chemical formula $(HSO_3)^-$. These salts also contain a cation and can be represented by the general chemical formula $XP^+_m(S_2O_5)^{2-}_n$ for metabisulfite salts, $XP^+_m(SO_3)^{2-}_n$ for sulfite salts, and $XP^+_m(HSO_3)^-_n$ for hydrogen sulfite salts wherein X corresponds to the cation, and m and n are integer values (i.e. 1, 2, 3, 4, etc.) representing the relative ratio of cations to anions in the salt, and p+ represents the value of the positive charge on the cation (i.e. +1, +2, +3, +4, etc.). It is well known to a chemist of ordinary skill in the art that in the general chemical formulas depicted for these salts, the values for m and n are such that the overall charge on the salt is neutral. For example, sodium metabisulfite can be represented by the chemical formula $Na_2S_2O_5$, wherein two sodium cations (each having a +1 charge) are present for each metabisulfite anion (having a −2 charge). Sodium sulfite can be represented by the chemical formula $Na_2SO_3$, wherein two sodium cations (each having a +1 charge) are present for each sulfite anion (having a −2 charge). Sodium hydrogen sulfite can be represented by the chemical formula $NaHSO_3$, wherein one sodium cation (having a +1 charge) is present for each hydrogen sulfite anion (having a −1 charge). Calcium metabisulfite can be represented by the chemical formula $CaS_2O_5$ wherein one calcium cation (having a +2 charge) is present for each metabisulfite anion (having a −2 charge). Aluminum metabisulfite can be represented by the chemical formula $Al_2(S_2O_5)_3$ wherein two aluminum cations (each having a +3 charge) are present for each three metabisulfite anions (each having a −2 charge). See also The Merck Index, Tenth Edition, (1983), Sodium Metabisulfite, Entry 8476, p. 1237, Sodium Sulfite, Entry 8528, p. 1242, and Sodium Bisulfite, Entry 8419, p. 1231, all of which are incorporated by reference herein in their entirety.

Metabisulfite, sulfite, and hydrogen sulfite salts useful herein include those selected from the group consisting of alkali metal salts (for example lithium, sodium, potassium, and the like), alkaline metal salts (for example beryllium, magnesium, calcium, and the like), ammonium salts, and mixtures thereof. The ammonium salts are defined herein to encompass those salts containing both the unsubstituted ammonium cation (i.e. $NH_4^+$) as well as various substituted ammonium cations. Nonlimiting examples of substituted ammonium cations include alkyl ammonium cations such as monoalkyl, dialkyl, trialkyl, and tetraalkyl ammonium cations wherein the alkyl groups are independently selected from straight and branched chain alkyl groups having from about 1 to about 30 carbon atoms. Other examples of substituted ammonium cations include alkanol ammonium cations such as monoalkanol, dialkanol, trialkanol, and tetraalkanol ammonium cations wherein the alkanol groups are independently selected from straight and branched chain alkanol groups having from about 2 to about 30 carbon atoms. Nonlimiting examples of substituted alkyl ammonium and alkanol ammonium cations include methyl ammonium, ethyl ammonium, dimethyl ammonium, diethyl ammonium, trimethyl ammonium, triethyl ammonium, tetramethyl ammonium, tetraethyl ammonium, dimethyl distearyl ammonium, monoethanol ammonium, diethanol ammonium, triethanol ammonium, tetraethanol ammonium, monoethanoltrimethyl ammonium cations, and mixtures thereof.

Among the metabisulfite, sulfite, and hydrogen sulfite salts useful herein, the metabisulfite salts are preferred. Preferred metabisulfite salts include those selected from the group consisting of sodium metabisulfite (i.e. $Na_2S_2O_5$), potassium metabisulfite (i.e. $K_2S_2O_5$), ammonium metabisulfite [i.e. $(NH_4)_2(S_2O_5)$], and mixtures thereof. Most preferred is sodium metabisulfite.

Topical Carrier

The compositions of the present invention comprise as an essential component a topical carrier or diluent which can be of a wide variety of different forms. The term "topical carrier" means a vehicle or base composition for containing, delivering, or carrying the essential components and any additional or optional components of the present invention to the surface of the skin. The topical carrier should be one that is pharmaceutically acceptable because of its intended use on human skin. The topical carrier can contain a wide variety of common pharmaceutical and cosmetic ingredients typically used in the beauty care industry, nonlimiting examples of which are described below. The topical carrier can be in the form of an emulsion including, but not limited to, oil-in-water, water-in-oil, water-in-oil-in-water, water-in-silicone and oil-in-water-in-silicone emulsions. These emulsions can cover a broad range of consistencies including thin lotions (which can also be suitable for aerosol or nonaerosol spray delivery), creamy lotions, light creams, heavy creams, and the like. The topical carrier can also comprise an aqueous-based system containing other water-soluble solvents such as alcohols. These aqueous-based systems can be formulated over a wide range of viscosities and can be thickened with a wide variety of water-compatible thickening agents to form viscous liquids and gels. The lower viscosity aqueous-based systems can also be delivered as aerosol and nonaerosol sprays. The viscosity of the compositions herein will therefore vary depending upon the exact ingredients chosen and the type of carrier desired. For example, the viscosity of the compositions herein can range from about 0.1 cps to about 5,000,000 cps, or more. Nonlimiting examples of topical carriers useful in the present invention are described in the following four references all of which are incorporated herein by reference in their entirety: "Sun Products Formulary" *Cosmetics & Toiletries*, vol. 105, pp. 122–139 (December 1990); "Sun Products Formulary", *Cosmetics & Toiletries*, vol. 102, pp. 117–136 (March 1987); U.S. Pat. No. 4,960,764 to Figueroa et al., issued Oct. 2, 1990; and U.S. Pat. No. 4,254,105 to Fukuda et al., issued Mar. 3, 1981.

The topical carrier can also comprise an oil-in-water emulsion system having complex structures such as liquid crystals and crystalline gel networks. The nature of liquid crystals, the formation of liquid crystals, and the properties and the advantages of liquid crystals are described further in G. Dahms, Properties of O/W Emulsions With Anisotropic Lamellar Phases, 101 *Cosmetics & Toiletries,* 113–115 (1986); P. Loll, Liquid Crystals in Cosmetic Emulsions, *ICI Surfactants' Publication RP94–93E*; and G. M. Eccleston, Multiple-Phase Oil-In-Water Emulsions, 41, J. Soc. Cosmet. Chem., 1–22, (January/February 1990); all of which are incorporated herein by reference in their entirety.

The exact level of the topical carrier employed will vary depending upon the carrier chosen, the levels of the essential components, and the levels of any optional components. The topical carrier comprises from about 50% to about 99.875%, preferably from about 70% to about 99%, and most preferably from about 75% to about 96%, of the compositions of the present invention.

pH Of The Compositions

Without being limited by theory, it is believed that pH can be a factor contributing to the chemical and physical stability of a composition containing dihydroxyacetone. For example, it is well known that dihydroxyacetone rapidly degrades at extremes of pH, and that at such extremes both the physical and chemical stability of the compositions can be adversely effected.

Although the compositions of the present invention can encompass a wide range of pH values, the compositions preferably have a pH from about 2.5 to about 7, more preferably from about 2.5 to about 6, and most preferably from about 3.5 to about 5. The pH will depend upon the combination of essential and optional ingredients chosen. An acidic buffer system can be useful, but is not required, in helping to maintain the desired pH of the compositions. Nonlimiting examples of acidic buffer systems useful herein include those selected from the group consisting of citrate, acetate, phosphate, and benzoate buffers.

It is well known to one of ordinary skill in the art that the pH of an aqueous system is readily measured utilizing pH meters and commercially available indicator papers. In the case of aqueous systems the pH value is readily made on the aqueous phase. In the case of primarily non-aqueous systems, e.g. in emulsion systems having a continuous oil phase (i.e. water-in-oil emulsions) the pH value would correspond to the internal water phase of such systems.

Additional Components

The compositions of the present invention can comprise a wide range of additional components. These additional components can comprise the topical carrier or can comprise components which are delivered from the topical carrier.

The *CTFA Cosmetic Ingredient Handbook*, Second Edition, 1992, which is incorporated by reference herein in its entirety, describes a wide variety of nonlimiting cosmetic and pharmaceutical ingredients commonly used in the beauty care industry, which are suitable for use in the compositions of the present invention. Nonlimiting examples of functional classes of these ingredients are described at page 537 of this reference. Examples of these functional classes include: abrasives, absorbents, antiacne agents, anticaking agents, antifoaming agents, antimicrobial agents, antioxidants, binders, biological additives, buffering agents, bulking agents, chelating agents, chemical additives, colorants, cosmetic astringents, cosmetic biocides, denaturants, drug astringents, emulsion stabilizers, external analgesics, film formers, fragrance components, humectants, opacifying agents, pH adjusters, preservatives, propellants, reducing agents, skin bleaching agents, skin-conditioning agents (emollients, humectants, miscellaneous, and occlusive), skin protectants, solvents, sunscreen agents, surfactants (cleansing agents, emulsifying agents, foam boosters, hydrotropes, solubilizing agents, suspending agents, and nonsurfactants), ultraviolet light absorbers, viscosity decreasing agent, and viscosity increasing agents (aqueous and nonaqueous).

Some nonlimiting examples of these additional components cited in the *CTFA Cosmetic Ingredient Handbook*, as well as other materials useful herein, include the following: vitamins and derivatives thereof (e.g tocopherol, tocopherol acetate, retinoic acid, retinol, retinoids, and the like); thickening agents; crosslinked acrylic acid homopolymers available as the carbomers from B.F. Goodrich; acrylates/C10–30 alkyl acrylate crosspolymers available as Carbopol 1342 from B.F. Goodrich; gums; waxes (both naturally occurring and synthetic); polymers for aiding the film-forming properties and substantivity of the composition (such as a copolymer of eicosene and vinyl pyrrolidone, an example of which is available from GAF Chemical Corporation as Ganex V-220$^R$); preservatives for maintaining the antimicrobial integrity of the compositions; skin penetration aids such as DMSO, 1-dodecylazacycloheptan-2-one (available as Azone from the Upjohn Co.) and the like; anti-acne medicaments (e.g., resorcinol, salicylic acid, erythromycin, benzoyl peroxide, zinc, and the like); skin bleaching (or lightening) agents including but not limited to hydroquinone, kojic acid; antioxidants; chelators and sequestrants; and aesthetic components such as fragrances, pigments, colorings, essential oils, skin sensates, astringents, skin soothing agents, skin healing agents and the like, nonlimiting examples of these aesthetic components include panthenol and derivatives (e.g. ethyl panthenol), aloe vera, pantothenic acid and its derivatives, clove oil, menthol, camphor, eucalyptus oil, eugenol, menthyl lactate, witch hazel distillate, allantoin, bisabolol, dipotassium glycyrrhizinate and the like; and skin conditioning agents such as the propoxylated glycerols described in U.S. Pat. No. 4,976,953, to Orr et al., issued Dec. 11, 1990, which is incorporated by reference herein in its entirety. Especially preferred optional ingredients include sunscreen agents and amino acids as further described below.

Sunscreen Agents

The compositions of the present invention can comprise one or more sunscreen agents. When a sunscreen agent is employed, it is found that the compositions of the present invention are also useful for protecting human skin from the harmful effects of ultraviolet radiation.

The sunscreen agent can comprise from about 0.1% to about 30%, more preferably from about 0.5% to about 25%, and most preferably from about 1% to about 20% of the compositions of the present invention. Exact amounts of sunscreen agent will vary depending upon the sunscreen or sunscreens chosen and the desired Sun Protection Factor (SPF) to be achieved. SPF is a commonly used measure of photoprotection of a sunscreen against erythema. The SPF is defined as the ratio of the ultraviolet energy required to produce minimal erythema on protected skin to that required to produce the same minimal erythema on unprotected skin in the same individual. *See Federal Register*, Vol. 43, No. 166, pp. 38206–38269, Aug. 25, 1978, which is incorporated herein by reference in its entirety.

A wide variety of sunscreen agents are useful herein. These sunscreen agents include both organic compounds and their salts as well as inorganic particulate materials. Without being limited by theory, it is believed that sunscreen agents provide protection from ultraviolet radiation by one or more of the following mechanisms including absorption, scattering, and reflection of the ultraviolet radiation. Nonlimiting examples of these sunscreen agents are described in U.S. Pat. No. 5,087,445, to Haffey et al., issued Feb. 11, 1992; U.S. Pat. No. 5,073,372, to Turner et al., issued Dec. 17, 1991; U.S. Pat. No. 5,073,371, to Turner et al. issued Dec. 17, 1991; U.S. Pat. No. 5,160,731, to Sabatelli et al., issued Nov. 3, 1992; U.S. Pat. No. 5,138,089, to Sabatelli, issued Aug. 11, 1992; U.S. Pat. No. 5,041,282, to Sabatelli, issued Aug. 20, 1991; U.S. Pat. No. 4,999,186, to Sabatelli et al., issued Mar. 12, 1991; U.S. Pat. No. 4,937,370, to Sabatelli, issued Jun. 26, 1990; and Segarin, et al., at Chapter VIII, pages 189 et seq., of *Cosmetics Science and Technology*; all of these documents being incorporated herein by reference in their entirety. Preferred among the sunscreen agents are those selected from the group consisting of 2-ethylhexyl p-methoxycinnamate, octyl salicylate, octocrylene, oxybenzone, 2-ethylhexyl N,N-dimethylaminobenzoate, paminobenzoic acid, 2-phenyl-benzimidazole-5-sulfonic acid, homomenthyl salicylate, DEA p-methoxycinnamate, 4,4' methoxy-t-butyldibenzoylmethane, 4-isopropyldibenzoylmethane, 3-(4methylbenzylidene) camphor, 3-benzylidene camphor, 4-N,N-dimethylaminobenzoic acid ester with 2,4-dihydroxybenzophenone, 4-N,N-dimethylaminobenzoic acid ester with 2-hydroxy-4-(2hydroxyethoxy)benzophenone, 4-N,N-dimethylaminobenzoic acid ester with 4-hydroxydibenzoyl-methane, 4-N,N-dimethylaminobenzoic acid ester with 4-(2-hydroxyethoxy)dibenzoylmethane, 4-N,N-di(2-ethylhexyl)aminobenzoic acid ester with 2,4-dihydroxybenzophenone, 4-N,N-di(2ethylhexyl)aminobenzoic acid ester with 2-hydroxy-4-(2hydroxyethoxy)benzophenone, 4-N,N-di(2-ethylhexyl)aminobenzoic acid ester with 4-hydroxydibenzoylmethane, 4-N,N-di(2ethylhexyl)aminobenzoic acid ester with 4-(2-hydroxyethoxy)dibenzoylmethane, 4-N,N-(2-ethylhexyl)methylaminobenzoic acid ester with 2,4-dihydroxybenzophenone, 4-N,N-(2ethylhexyl)methylaminobenzoic acid ester with 2-hydroxy-4-(2hydroxyethoxy)benzophenone, 4-N,N-(2-ethylhexyl)methylaminobenzoic acid ester with 4-hydroxydibenzoylmethane, 4-N,N-(2-ethylhexyl)methylaminobenzoic acid ester with 4-(2-hydroxyethoxy)dibenzoylmethane, titanium dioxide, zinc oxide, iron oxide, and mixtures thereof.

More preferred for use in the compositions described herein are the sunscreen agents selected from the group consisting of 2-ethylhexyl N,N-dimethyl-p-aminobenzoate, 2-ethylhexyl p-methoxycinnamate, octocrylene, octyl salicylate, homomenthyl salicylate, p-aminobenzoic acid, oxybenzone, 2-phenylbenzimidazole-5-sulfonic acid, DEA pmethoxycinnamate, 4,4' -methoxy-t-butyldibenzoylmethane, 4-isopropyl dibenzoylmethane, 3-(4-methylbenzylidene) camphor, 3-benzylidene camphor, 4-N,N-(2-ethylhexyl)methylaminobenzoic acid ester with 4-(2hydroxyethoxy)dibenzoylmethane, titanium dioxide, zinc oxide, iron oxide, and mixtures thereof.

Most preferred for use in the compositions described herein are the sunscreen agents selected from the group consisting of 2-ethylhexyl N,N-dimethyl-p-aminobenzoate, 2-ethylhexyl p-methoxycinnamate, octocrylene, octyl salicylate, oxybenzone, 2-phenylbenzimidazole-5-sulfonic acid, 4,4' -methoxy-t-buyldibenzoylmethane, 3-(4methylbenzylidene) camphor, 3-benzylidene camphor, 4-N,N-(2ethylhexyl)methylaminobenzoic acid ester with 4-(2-hydroxyethoxy)dibenzoylmethane, titanium dixoide, zinc oxide, iron oxide, and mixtures thereof.

Amino Acids and Pharmaceutically Acceptable Salts

The compositions of the present invention can also comprise an amino acid, or a pharmaceutically acceptable salt thereof selected from the group consisting of alanine, valine, leucine, isoleucine, proline, methionine, phertylalanine, tryptophan, glycine, serine, threonine, cysteine, tyrosine, asparagine, glutamine, lysine, arginine, histidine, and mixtures thereof. These amino acids or their pharamaceutically acceptable salts comprise from about 0.1% to about 10%, more preferably from about 0.25% to about 5%, and most preferably from about 0.50% to about 1.5% of the compositions herein.

Amino acids and their pharmaceutically acceptable salts described herein are useful for modifying the artificial tan color obtained on human skin using dihydroxyacetone. Dihydroxyacetone is known to react with various nitrogen containing compounds to produce a brown or tan color. See, e.g. Kawashima et al., "Nonenzymatic Browning Reactions of Dihydroxyacetone With Amino Acids or Their Esters", *Agric. Biol. Chem.* 44(7), 1595–1599 (1980), and M. F. Bobin et al., "Effects of Color Adjuvants On the Tanning Effect of Dihydroxyacetone", *J. Soc. Cosmet. Chem.*, 35 265–272 (August 1984), both of which are incorporated by reference herein in their entirety. However, this reaction, has previously been difficult to control and has been an obstacle to formulating a stable artificial tanning composition (i.e. especially one that is resistant to developing off-odors and discoloration) containing both dihydroxyacetone and an amino acid or a salt thereof. A possible solution to this incompatibility problem is to formulate the dihydroxyacetone separately from the amino acid and to either deliver the formulations sequentially from separate containers or simultaneously from a dual-chambered dispensing device. However, these alternatives are inconvenient, cumbersome, and expensive. See, e.g. European Patent No. 527,864, assigned to Unilever, published Jun. 23, 1993. In the stabilized compositions of the present invention, it is found that the amino acids or their pharmaceutically acceptable salts can be formulated without the incompatibility problems previously encountered.

As described above, the amino acids or their pharmaceutically acceptable salts thereof useful herein are those selected from the group consisting of alanine, valine, leucine, isoleucine, proline, methionine, phenylalanine, tryptophan, glycine, serine, threonine, cysteine, tyrosine, asparagine, glutamine, lysine, arginine, histidine, and mixtures thereof. Preferred are those selected from the group consisting of lysine, arginine, histidine, and mixtures thereof. Most preferred is the amino acid lysine and its pharmaceutically acceptable salts.

Lysine, or a pharmaceutically acceptable salt thereof, is most preferred for use herein, because of the especially natural looking and rapidly developing artificial tan obtained from the addition of this material to a dihydroxyacetone containing composition. Lysine is one of the commonly occurring amino acids and is also known as 2,6diaminohexanoic acid. Lysine contains two amino groups and a single carboxylic acid group and can be represented by the chemical formula $C_6H_{14}N_2O_2$ and the following chemical structure.

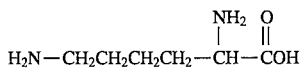

See *The Merck Index*, Tenth Edition, Entry 5453, page 806 (1983), which is incorporated herein by reference in its entirety. Lysine is a compound having a chiral center at the two carbon position and can therefore exist in either the (R) or (S) enatiomeric form. Traditionally, amino acid stereochemistry is also defined in terms of D and L configurations, as is commonly done for carbohydrates. The naturally occurring form of lysine is the L enantiomer, which corresponds to the (S) configuration. The lysine molecule can form salts at its carboxylic acid group with cationic species and at either one or both of its amino groups with anionic species. Because the lysine molecule contains a carboxylic acid group and two amino groups, the molecule therefore exhibits three $pK_a$ values at 2.16, 9.20, and 10.80. It is believed that these $pK_a$ values correspond to the carboxylic acid group, the amino group at the two carbon position, and the amino group at the six carbon position, respectively. The pH of the medium in which the lysine is present will therefore determine whether any of these sites will be in their neutral or ionic form. See A. Streitwieser, Jr. and C. H. Heathcock, *Introduction to Organic Chemistry*, Chapter 28, pp. 814–860, Macmillan Pub. Co., Inc., N.Y., 1976, which is incorporated herein by reference in its entirety.

As described above, most preferred among the amino acids are lysine and its pharmaceutically acceptable salts. Nonlimiting examples of pharmaceutically acceptable lysine salts include lysine sodium salt, lysine potassium salt, lysine calcium salt, lysine magnesium salt, lysine hydrochloride, lysine dihydrochloride, lysine succinate, lysine phosphate, lysine hydrogen sulfate, lysine di(hydrogen sulfate), lysine carbonate, lysine hydrogen carbonate, lysine di(hydrogen carbonate), and mixtures thereof. It is found that among these salts that lysine hydrochloride and lysine dihydrochloride are preferred.

Methods for Providing an Artificial Tan and for Protecting the Skin from UV Radiation The compositions of the present invention are useful for providing an artificial tan to human skin. These compositions, when optionally formulated to contain sunscreen compounds as described above, are also useful for protecting human skin from the harmful effects of ultraviolet radiation. To obtain an artificial tan and/or protection from the harmful effects of UV radiation, an effective amount of the composition of the present invention is applied to the skin. The term "effective" means an amount of the present composition to provide an artificial tan and/or protection from ultraviolet radiation, but not so much as to cause any undesirable side effects or skin reactions. The term "protection" means that the present compositions attenuate or reduce the amount of ultraviolet radiation reaching the skin's surface thereby reducing the incidence of undesirable skin reactions such as sunburn, erythema, skin cancer, and photoinduced skin aging. As described above, one commonly used measure of a compositions effectiveness against ultraviolet radiation is the SPF factor.

A wide range of quantities of the compositions of the present invention can be employed to provide an artificial tan and/or protection from the harmful effects of ultraviolet radiation. Quantities of the present compositions which are typically applied to provide an artificial tan and/or protection from the harmful effects of ultraviolet radiation typically range from about 0.1 m/cm$^2$ to about 10 mg/cm$^2$. A particularly useful amount to use is about 2 mg/cm$^2$.

EXAMPLES

The following examples further describe and demonstrate embodiments within the scope of the present invention. The examples are given solely for the purpose of illustration and are not to be construed as limitations of the present invention, as many variations thereof are possible without departing from the spirit and scope of the invention.

Ingredients are identified by chemical or CTFA name.

EXAMPLES I–III

Artificial Tanning Creams

An oil-in-water emulsion is prepared by combining the following ingredients using conventional mixing techniques. Examples I, II, and III correspond to light, medium, and dark artificial tanning creams, respectively.

| Examples Ingredients | I | II | III |
|---|---|---|---|
| | | Weight Percent | |
| PHASE A | | | |
| Water | qs 100 | qs 100 | qs 100 |
| Glycerin | 5.00 | 5.00 | 5.00 |
| Magenisum Aluminum Silicate | 0.50 | 0.50 | 0.50 |
| Xanthan Gum | 0.30 | 0.30 | 0.30 |
| Disodium EDTA | 0.10 | 0.10 | 0.10 |
| PHASE B | | | |
| Cyclomethicone | 3.00 | 3.00 | 3.00 |
| Cetyl Alcohol | 2.00 | 2.00 | 2.00 |
| Stearyl Alcohol | 2.00 | 2.00 | 2.00 |
| Steareth-20 | 1.00 | 1.00 | 1.00 |
| Polysorbate 60 | 0.50 | 0.50 | 0.50 |
| Dimethicone Copolyol | 0.50 | 0.50 | 0.50 |
| Glyceryl Stearate (and) PEG-100 Stearate | 0.25 | 0.25 | 0.25 |
| PHASE C | | | |
| Water | 8.00 | 9.00 | 11.0 |
| Dihydroxyacetone | 4.00 | 5.00 | 6.00 |
| Sodium Metabisulfite | 0.25 | 0.25 | 0.25 |
| Phase D | | | |
| Water | 2.50 | 2.50 | 2.50 |
| Butylene Glycol | 2.50 | 2.50 | 2.50 |
| DMDM Hydantoin (and) Iodopropynyl Butylcarbamate | 0.25 | 0.25 | 0.25 |
| Sorbic Acid | 0.10 | 0.10 | 0.10 |
| PHASE E | | | |
| Fragrance | 0.15 | 0.15 | 0.15 |

In a suitable vessel the Phase A ingredients are dispersed in the water with stirring and heated to 70°–75° C. In a separate vessel the Phase B ingredients are combined and heated to 70°–75° C. and maintained until all ingredients are melted. Phase B is slowly added to Phase A and the resulting emulsion is stirred for 15 minutes while maintaining a temperature of 70°–75° C. The emulsion is then allowed to cool to 40° C. In a separate vessel the ingredients of Phase C are added and stirred until dissolved. When the emulsion is at or below 40° C., Phase C is added. In a separate vessel the ingredients of Phase D are added, stirred and warmed to 40° C. until all are dissolved. Phase D is next added and stirring is continued for 15 minutes. When the emulsion is at 35° C., Phase E is added, and stirring is continued until cooled to room temperature.

The resulting sunless tanning creams exhibit good physical and chemical stability and are useful for topical application to human skin to provide an artificial tan.

In variations on these formulas the sodium metabisulfite level is varied over the range from about 0.025% to about 5%. In further variations, the sodium metabisulfite is replaced with an equal weight of sodium sulfite, sodium bisulfite, potassium metabisulfite, or ammonium metabisulfite.

EXAMPLES IV–VI

Artificial Tanning Creams Containing Sunscreens

An oil-in-water emulsion is prepared by combining the following ingredients using conventional mixing techniques. Examples IV, V, and VI correspond to light, medium, and dark artificial tanning creams, respectively.

| Examples Ingredients | IV | V | VI |
|---|---|---|---|
| | | Weight Percent | |
| PHASE A | | | |
| Water | qs 100 | qs 100 | qs 100 |
| Glycerin | 5.00 | 5.00 | 5.00 |
| Magenisum Aluminum Silicate | 0.50 | 0.50 | 0.50 |
| Xanthan Gum | 0.30 | 0.30 | 0.30 |
| Disodium EDTA | 0.10 | 0.10 | 0.10 |
| PHASE B | | | |
| 2-Ethylhexyl p-Methoxycinnamate | 2.00 | 2.00 | 2.00 |
| Cyclomethicone | 3.00 | 3.00 | 3.00 |
| Cetyl Alcohol | 2.00 | 2.00 | 2.00 |
| Stearyl Alcohol | 2.00 | 2.00 | 2.00 |
| Steareth-20 | 1.00 | 1.00 | 1.00 |
| Octocrylene | 1.00 | 0.00 | 0.00 |
| Oxybenzone | 1.00 | 0.00 | 0.00 |
| Polysorbate 60 | 0.50 | 0.50 | 0.50 |
| Dimethicone Copolyol | 0.50 | 0.50 | 0.50 |
| Glyceryl Stearate (and) PEG-100 Stearate | 0.25 | 0.25 | 0.25 |
| PHASE C | | | |
| Water | 8.00 | 9.00 | 11.0 |
| Dihydroxyacetone | 4.00 | 5.00 | 6.00 |
| Sodium Metabisulfite | 0.25 | 0.25 | 0.25 |
| Phase D | | | |
| Water | 2.50 | 2.50 | 2.50 |
| Butylene Glycol | 2.50 | 2.50 | 2.50 |
| DMDM Hydantoin (and) Iodopropynyl Butylcarbamate | 0.25 | 0.25 | 0.25 |
| Sorbic Acid | 0.10 | 0.10 | 0.10 |
| PHASE E | | | |
| Fragrance | 0.15 | 0.15 | 0.15 |

In a suitable vessel the Phase A ingredients are dispersed in the water with stirring and heated to 70°–75° C. In a separate vessel the Phase B ingredients are combined and heated to 70°–75° C. and maintained until all ingredients are melted. Phase B is slowly added to Phase A and the resulting emulsion is stirred for 15 minutes while maintaining a temperature of 70°–75° C. The emulsion is then allowed to cool to 40° C. In a separate vessel the ingredients of Phase C are added and stirred until dissolved. When the emulsion is at or below 40° C, Phase C is added. In a separate vessel the ingredients of Phase D are added, stirred and warmed to 40° C. until all are dissolved. Phase D is next added and stirring is continued for 15 minutes. When the emulsion is at 35° C., Phase E is added and stirring is continued for 5 minutes followed by cooling to room temperature.

The resulting sunless tanning creams exhibit good physical and chemical stability and are useful for topical application to human skin to provide an artificial tan and to provide protection from the harmful effects of ultraviolet radiation.

In variations on these formulas the sodium metabisulfite level is varied over the range from about 0.025% to about 5%. In further variations, the sodium metabisulfite is replaced with an equal weight of sodium sulfite, sodium bisulfite, potassium metabisulfite, or ammonium metabisulfite.

13
EXAMPLES VII–VIII

Artificial Tanning Creams

An oil-in-water emulsion is prepared by combining the following ingredients using conventional mixing techniques. Examples VII and VIII correspond to non-sunscreen and sunscreen-containing formulas respectively.

| Examples<br>Ingredients | VII | VIII |
|---|---|---|
| | Weight Percent | |
| Phase A | | |
| Water | qs 100 | qs 100 |
| Cetyl Hydroxyethylcellulose | 0.50 | 0.50 |
| Disodium EDTA | 0.030 | 0.03 |
| Phase B | | |
| PPG-15 Stearyl Ether | 11.0 | 0 |
| 2-Ethylhexyl p-Methoxycinnamate | 0 | 2.00 |
| Oxybenzone | 0 | 1.00 |
| Octocrylene | 0 | 1.00 |
| Dimethicone & Trimethylsiloxysilicate | 2.00 | 2.00 |
| Dimethicone | 1.00 | 1.00 |
| Glyceryl Stearate | 2.60 | 2.60 |
| PVP/Eicosene Copolymer | 0.80 | 0.80 |
| Cetyl Alcohol | 0.75 | 0.75 |
| Stearyl Alcohol | 0.50 | 0.50 |
| Ceteareth-12 | 0.50 | 0.50 |
| Ceteareth-20 | 0.50 | 0.50 |
| Phase C | | |
| Water | 2.00 | 2.00 |
| Butylene Glycol | 2.00 | 2.00 |
| DMDM Hydantoin (and) Iodopropynyl Butylcarbamate | 0.20 | 0.20 |
| Phase D | | |
| Water | 6.00 | 6.00 |
| Dihydroxyacetone | 3.00 | 3.00 |
| Sodium Metabisulfite | 0.25 | 0.25 |
| Phase E | | |
| Fragrance | 1.00 | 1.00 |

In a suitable vessel the Phase A ingredients are dispersed in the water and heated to 75°–85° C. In a separate vessel the Phase B ingredients are combined and heated to 85°–90° C. until melted and this mixture is then added to Phase A to form the emulsion. The emulsion is cooled to 40°–45° C. with continued mixing. In a separate vessel, the Phase C ingredients are combined and the resulting solution is mixed into the emulsion. In a separate vessel, the dihydroxyacetone is dissolved in water to form Phase D, and the resulting solution is mixed into the emulsion. Finally, the fragrance, Phase E, is added to the emulsion with mixing, which is then cooled to 30°–35° C., and then to room temperature.

These emulsions have improved stability and are useful for topical application to the skin to provide an artificial tan and/or protection from ultraviolet radiation.

In variations on these formulas the sodium metabisulfite level is varied over the range from about 0.025% to about 5%. In further variations, the sodium metabisulfite is replaced with an equal weight of sodium sulfite, sodium bisulfite, potassium metabisulfite, or ammonium metabisulfite.

14
EXAMPLE IX

ARTIFICIAL TANNING GEL

An artificial tanning gel is prepared utilizing conventional mixing techniques.

| Ingredients | Weight Percent |
|---|---|
| Water | qs |
| Dihydroxyacetone | 3.00 |
| Glycerin | 3.00 |
| Polysorbate 20 | 1.00 |
| Triethanolamine | 0.50 |
| Carbomer 940 | 0.40 |
| DMDM Hydantoin | 0.10 |
| IsopropylC12–15 Pareth-9 Carboxylate | 0.10 |
| Diazolidinyl Urea | 0.10 |
| Disodium EDTA | 0.05 |
| Fragrance | 0.30 |
| Sodium Metabisulfite | 0.25 |

In a suitable vessel, all ingredients except the triethanolamine and 1% of the water are combined with stirring. The triethanolamine and remaining 1% water are combined in a separate vessel, and then slowly added to the rest of the mixture while stirring is continued.

The resulting artificial tanning gel has improved stability and is useful for topical application to the skin to provide an artificial tan.

In variations on these formulas the sodium metabisulfite level is varied over the range from about 0.025% to about 5%. In further variations, the sodium metabisulfite is replaced with an equal weight of sodium sulfite, sodium bisulfite, potassium metabisulfite, or ammonium metabisulfite.

EXAMPLE X

ARTIFICIAL TANNING SPRAY

An artificial tanning spray is prepared utilizing conventional mixing techniques.

| Ingredients | Weight Percent |
|---|---|
| Water | qs 100 |
| Dihydroxyacetone | 3.00 |
| Sodium Metabisulfite | 0.25 |
| Dimethylisosorbide | 3.00 |
| Glycereth-7 Triaceate | 1.00 |
| PEG-15 Laurate | 0.50 |
| Propylene Glycol | 1.00 |
| Methylparaben | 0.10 |
| Propylparaben | 0.10 |
| Glycerin | 3.00 |
| Polysorbate 20 | 1.00 |

In a suitable vessel, all ingredients are combined and mixed until uniform.

The resulting artificial tanning spray has improved stability and can be packaged in either a conventional non-aerosol pump spray bottle or can be combined with conventional propellant ingredients and packaged in an aerosol canister for topical application to the skin to provide an artificial tan.

In variations on these formulas the sodium metabisulfite level is varied over the range from about 0.025% to about 5%. In further variations, the sodium metabisulfite is replaced with an equal weight of sodium sulfite, sodium bisulfite, potassium metabisulfite, or ammonium metabisulfite.

EXAMPLES XI–XIII

Artificial Tanning Gel Network Emulsions Containing Dihydroxyacetone and Lysine Hydrochloride An oil-in-water emulsion is prepared by combining the following ingredients using conventional mixing techniques. Examples XI, XII, and XIII correspond to light, medium, and dark artificial tanning creams, respectively.

| Examples<br>Ingredients | XI | XII<br>Weight Percent | XIII |
|---|---|---|---|
| PHASE A | | | |
| Water | qs 100 | qs 100 | qs 100 |
| Glycerin | 5.00 | 5.00 | 5.00 |
| Cetyl Hydroxyethylcellulose | 0.15 | 0.15 | 0.15 |
| Disodium EDTA | 0.10 | 0.10 | 0.10 |
| Xanthan Gum | 0.10 | 0.10 | 0.10 |
| PHASE B | | | |
| Cetyl Alcohol | 2.13 | 2.13 | 2.13 |
| Behenyl Alcohol | 2.13 | 2.13 | 2.13 |
| Isohexadecane | 1.00 | 1.00 | 1.00 |
| PPG-3 Myristyl Ether | 1.00 | 1.00 | 1.00 |
| Cyclomethicone D5 | 1.00 | 1.00 | 1.00 |
| Ceteareth-20 | 0.45 | 0.45 | 0.45 |
| Ceteareth-12 | 0.30 | 0.30 | 0.30 |
| PHASE C | | | |
| Water | 9.00 | 10.00 | 12.00 |
| Dihydroxyacetone | 3.30 | 4.30 | 5.30 |
| Butylene Glycol | 2.50 | 2.50 | 2.50 |
| L-Lysine Hydrochloride | 0.75 | 0.75 | 0.75 |
| DMDM Hydantoin (and)<br>Iodopropynyl Butylcarbamate | 0.25 | 0.25 | 0.25 |
| Sodium Metabisulfite | 0.25 | 0.35 | 0.45 |
| PHASE D | | | |
| Fragrance | 0.15 | 0.15 | 0.15 |

In a suitable vessel the Phase A ingredients are dispersed in the water with stirring and heated to 70°–75° C. In a separate vessel the Phase B ingredients are combined and heated to 70°–75° C. and maintained until all ingredients are melted. Phase B is slowly added to Phase A and the resulting emulsion is homogenized for 15 minutes while maintaining a temperature of 70°–75° C. The emulsion is then allowed to cool to 40° C. In a separate vessel the ingredients of Phase C are added and stirred until all are dissolved. Phase C is next added and the emulsion is stirred for 15 minutes. When the emulsion is at 35° C., Phase D is added and stirring is continued until to cooled to room temperature.

The resulting compositions exhibit good physical and chemical stability, improved color development characteristics, and are useful for topical application to human skin to provide an artificial tan.

In variations on these formulas the sodium metabisulfite level is varied over the range from about 0.025% to about 5%. In further variations, the sodium metabisulfite is replaced with an equal weight of sodium sulfite, sodium bisulfite, potassium metabisulfite, or ammonium metabisulfite.

In further variations on these formulas the L-lysine hydrochloride is varied over the range from about 0.5% to about 1.5% by weight of the total composition. In further variations, the L-lysine hydrochloride is replaced with an equivalent weight of L-lysine or L-lysine dihydrochloride or other amino acids or their pharmaceutically acceptable salts such as arginine and histidine.

What is claimed is:

1. An artificial tanning composition having improved stability comprising:

(a) from about 0.1% to about 20% dihydroxyacetone,
   (b) from about 0.025% to about 5% of a salt selected from the group consisting of metabisulfite salts, sulfite salts, hydrogen sulfite salts, and mixtures thereof, and
   (c) a topical carrier.

2. A composition according to claim 1 wherein said metabisulfite, sulfite, and hydrogen sulfite salts are selected from the group consisting of alkali metal salts, alkaline metal salts, ammonium salts, and mixtures thereof.

3. A composition according to claim 1 wherein said metabisulfite, sulfite, and hydrogen sulfite salts are selected from the group consisting of sodium salts, potassium salts, ammonium salts, and mixtures thereof.

4. A composition according to claim 1 wherein said salt is a metabisulfite salt.

5. A composition according to claim 4 wherein said metabisulfite salt is selected from the group consisting of alkali metal metabisulfite salts, alkaline metal metabisuflte salts, ammonium metabisulfite salts, and mixtures thereof.

6. A composition according to claim 5 wherein said metabisulfite salt is selected from the group consisting of sodium metabisulfite, potassium metabisulfite, ammonium metabisulfite, and mixtures thereof.

7. A composition according to claim 6 wherein said metabisulfite salt is sodium metabisulfite.

8. A composition according to claim 4 comprising from about 0.05% to about 5% of said metabisulfite salt.

9. A composition according to claim 4 comprising from about 0.05% to about 1% of said metabisuflte salt.

10. A composition according to claim 4 comprising from about 0.1% to about 1% of said metabisulfite salt.

11. A composition according to claim 4 comprising about 0.25% of said metabisulfite salt.

12. A composition according to claim 11 comprising from about 2% to about 7% dihydroxyacetone.

13. A composition according to claim 11 comprising from about 3% to about 6% dihydroxyacetone.

14. A composition according to claim 1 wherein said composition further comprises from about 0.5% to about 20% of a sunscreen selected from the group consisting of 2-ethylhexyl N,N-dimethyl-p-aminobenzoate, 2-ethylhexyl p-methoxycinnamate, octocrylene, octyl salicylate, oxybenzone, 2-phenylbenzimidazole-5-sulfonic acid, 4,4'-methoxy-t-buyldibenzoylmethane, 3-(4-methylbenzylidene) camphor, 3-benzylidene camphor, 4-N,N-(2-ethylhexyl)methylaminobenzoic acid ester with 4-(2-hydroxyethoxy-)dibenzoylmethane, titanium dioxide, zinc oxide, iron oxide, and mixtures thereof.

15. A composition according to claim 1 wherein said composition further comprises from about 0.1% to about 10% of an amino acid or pharmaceutically acceptable salt thereof selected from the group consisting of alanine, valine, leucine, isoleucine, proline, methionine, phenylalanine, tryptophan, glycine, serine, threonine, cysteine, tyrosine, asparagine, glutamine, lysine, arginine, histidine, and mixtures thereof.

16. A composition according to claim 1 wherein said composition further comprises from about 0.1% to about 10% of an amino acid or a pharmaceutically acceptable salt thereof selected from the group consisting of lysine, arginine, histidine, and mixtures thereof.

17. A composition according to claim 1 wherein said composition further comprises from about 0.1% to about 10% of an amino acid or a pharmaceutically accetable salt thereof selected from the group consisting of L-lysine, L-lysine hydrochloride, L-lysine dihydrochloride, and mixtures thereof.

18. A method for providing an artificial tan to human skin topically applying to the skin an effective amount of a composition according to claim 1.

19. A method for providing an artificial tan to human skin and protecting human skin from the harmful effects of ultraviolet radiation comprising topically applying to the skin an effective amount of a composition according to claim 14.

* * * * *

UNITED STATES PATENT AND TRADEMARK OFFICE
CERTIFICATE OF CORRECTION

PATENT NO. : 5,514,437

DATED : May 7, 1996

INVENTOR(S) : Paul R. Tanner et al.

It is certified that error appears in the above-identified patent and that said Letters Patent is hereby corrected as shown below:

At column 4, lines 31-32 "$XP^+{}_m(S_2O_5)^{2-}{}_n$," should read --$X^{P+}{}_m(S_2O_5)^{2-}{}_n$--.

At column 4, line 32 "$XP^+{}_m(SO_3)^{2-}{}_n$," should read --$X^{P+}{}_m(SO_3)^{2-}{}_n$--.

At column 4, line 33 "$XP^+{}_m(HSO_3)^-{}_n$," should read --$X^{P+}{}_m(HSO_3)^-{}_n$--.

At column 6, line 10 "Lameliar" should read --Lamellar--.

At column 7, line 10 "agent" should read --agents--.

At column 8, line 22 "paminobenzoic" should read --p-aminobenzoic--.

At column 8, line 25 "3-(4methylbenzylidene)" should read --3-(4-methylbenzylidene)--.

At column 8, line 29 "2-hydroxy-4-(2hydroxyethoxy)" should read --2-hydroxy-4-(2-hydroxyethoxy)--.

At column 8, line 34 "4-N,N-di(2ethylhexyl)" should read --4-N,N-di(2-ethylhexyl)--.

At column 8, line 35 "2-hydroxy-4-(2hydroxyethoxy)" should read --2-hydroxy-4-(2-hydroxyethoxy)--.

At column 8, lines 37-38 "4-N,N-di(2ethylhexyl)" should read --4-N,N-di(2-ethylhexyl)--.

At column 8, line 41 "4-N,N-(2ethylhexyl)" should read --4-N,N-(2-ethylhexyl)--.

At column 8, line 42 "2-hydroxy-4-(2hydroxyethoxy)" should read --2-hydroxy-4-(2-hydroxyethoxy)--.

At column 8, line 54 "pmethoxycinnamate" should read --p-methoxycinnamate--.

At column 8, line 58 "4-(2hydroxyethoxy)" should read --4-(2-hydroxyethoxy)--.

At column 8, lines 65-66 "3-(4methylbenzylidene)" should read --3-(4-methylbenzylidene)--.

At column 8, lines 66-67 "4-N,N-(2ethylhexyl)" should read --4-N,N-(2-ethylhexyl)--.

UNITED STATES PATENT AND TRADEMARK OFFICE
CERTIFICATE OF CORRECTION

PATENT NO. : 5,514,437

DATED : May 7, 1996

INVENTOR(S) : Paul R. Tanner et al.

It is certified that error appears in the above-identified patent and that said Letters Patent is hereby corrected as shown below:

At column 9, line 7 "phertylalanine" should read --phenylalanine--.

At column 9, line 57 "2,6diaminohexanoic" should read --2,6-diaminohexanoic--.

At column 10, line 60 "0.1 m/cm$^2$" should read --0.1 mg/cm$^2$--.

Signed and Sealed this

Ninth Day of March, 1999

Attest:

Q. TODD DICKINSON

Attesting Officer

Acting Commissioner of Patents and Trademarks